US010119898B2

(12) United States Patent
Huang et al.

(10) Patent No.: US 10,119,898 B2
(45) Date of Patent: Nov. 6, 2018

(54) PARTICLE SCREENING DEVICE

(71) Applicant: Pixel Biotech (Shanghai) Co., Ltd., Shanghai (CN)

(72) Inventors: Chengjun Huang, Beijing (CN); Jun Luo, Beijing (CN); Chao Zhao, Beijing (CN)

(73) Assignee: Pixel Biotech (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 15/326,425

(22) PCT Filed: Jun. 24, 2015

(86) PCT No.: PCT/CN2015/082196
§ 371 (c)(1),
(2) Date: Jan. 13, 2017

(87) PCT Pub. No.: WO2016/011869
PCT Pub. Date: Jan. 28, 2016

(65) Prior Publication Data
US 2017/0205330 A1    Jul. 20, 2017

(30) Foreign Application Priority Data
Jul. 22, 2014    (CN) .......................... 2014 1 0350710

(51) Int. Cl.
*G01N 15/10*    (2006.01)
*B01L 3/00*    (2006.01)
(Continued)

(52) U.S. Cl.
CPC ...... *G01N 15/1056* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS

| 9,039,883 B2 | 5/2015 | Guerrieri et al. |
| 2008/0227664 A1 | 9/2008 | Honma |
| | | (Continued) |

FOREIGN PATENT DOCUMENTS

| CN | 101135680 | 3/2008 |
| CN | 101460253 | 6/2009 |
| | (Continued) | |

OTHER PUBLICATIONS

International Search Report and Written Opinion dated Sep. 2, 2015 in Int'l App. No. PCT/CN2015/082196.
(Continued)

*Primary Examiner* — Arun S Phasge
(74) *Attorney, Agent, or Firm* — Knobbe Martens Olson & Bear LLP

(57) ABSTRACT

A particle screening device is provided. The particle screening device comprises: a substrate including a first side and a second side opposite to the first side; a micropore array formed on the substrate, wherein each micropore penetrates through the substrate from the first side to the second side and has a size configured to at least permit particles smaller than target particles flow through; and electrodes formed on at least one side of the first and second sides of the substrate and around at least some micropores, wherein the electrodes are configured to generate an electric field at corresponding micropores.

16 Claims, 3 Drawing Sheets

(51) Int. Cl.
*G01N 33/574* (2006.01)
*G01N 15/00* (2006.01)

(52) U.S. Cl.
CPC .... *B01L 3/502761* (2013.01); *G01N 15/1031* (2013.01); *G01N 33/574* (2013.01); *B01L 2200/0652* (2013.01); *B01L 2300/0645* (2013.01); *B01L 2300/0887* (2013.01); *B01L 2400/0424* (2013.01); *G01N 2015/0065* (2013.01); *G01N 2015/1006* (2013.01); *G01N 2015/1081* (2013.01); *G01N 2015/1087* (2013.01)

(56) References Cited

U.S. PATENT DOCUMENTS

| | | |
|---|---|---|
| 2012/0058504 A1 | 3/2012 | Li et al. |
| 2013/0261021 A1 | 10/2013 | Bocchi et al. |
| 2014/0158540 A1* | 6/2014 | Ohura .............. G01N 33/48721 204/543 |

FOREIGN PATENT DOCUMENTS

| | | |
|---|---|---|
| CN | 103392124 | 11/2013 |
| WO | WO 1990/004645 | 5/1990 |
| WO | WO 2007/138464 | 12/2007 |
| WO | WO 2012/054904 A3 | 4/2012 |
| WO | WO 2012/072822 | 6/2012 |
| WO | WO 2013/158021 A1 | 10/2013 |

OTHER PUBLICATIONS

Extended European Search Report, dated Feb. 21, 2018, issued in European Application No. 15824873.2.

* cited by examiner

PARTICLE SCREENING DEVICE

CROSS-REFERENCE TO RELATED APPLICATIONS

This application is the U.S. National Phase under 35 U.S.C. § 371 of International Application PCT/CN2015/082196, filed Jun. 24, 2015, which claims priority to Chinese Patent Application No. 201410350710.7 entitled "Particle Screening Device" filed on Jul. 22, 2014, which is incorporated herein by reference in its entirety.

TECHNICAL FIELD

The present disclosure generally relates to particle classification and detection, and in particular, to a particle screening device.

BACKGROUND

In life science research and medical examination, it is generally necessary to detect a component of interest which has extremely small content in samples, for example, Circulating Tumor Cells (CTCs) in human peripheral blood. CTCs are tumor cells which enter into peripheral blood circulation of cancer patients spontaneously or by clinical operation. Detection of tumor cells in peripheral blood may forebode tumor metastasis. It has been proven in current research that CTCs can predict progression free survival and overall survival for various tumors including breast carcinoma, prostate carcinoma, colon carcinoma, lung carcinoma, ovarian carcinoma, etc., reveal metastasis mechanism of tumors, and may have potential clinical significance in tumor staging, diagnosis and making therapeutic scheme. However, on the other hand, CTCs have extremely small amount in peripheral blood compared with erythrocytes and leukocytes. For example, there may exist one CTC per 5-10 million healthy blood cells. Therefore, such content of interest as CTC is so scanty that it is important to provide an enriching and detecting technique.

SUMMARY OF INVENTION

One object of the present disclosure is partially to provide a particle screening device to achieve target particle detecting with low cost and high efficiency.

In an embodiment of the present disclosure, a particle screening device is provided. The particle screening device comprises: a substrate including a first side and a second side opposite to the first side; a micropore array formed on the substrate, wherein each micropore penetrates through the substrate from the first side to the second side and has a size configured to at least permit particles smaller than target particles flow through; and electrodes formed on at least one side of the first and second sides of the substrate and around at least some micropores, wherein the electrodes are configured to generate an electric field at corresponding micropores.

The particle screening device according to an embodiment of the present disclosure can be manufactured by, for example, (silicon) Micro-Electro-Mechanical System (MEMS) technique. In one embodiment of the present disclosure, target particles can be screened with high efficiency by means of difference in size, dielectric response, etc. between the target particles and other particles. Further, cost can be reduced in screening since reagent or markers are not necessary.

DESCRIPTION OF DRAWINGS

The above and other objects, features, and advantages of the present disclosure will become more apparent from the following descriptions of embodiments thereof with reference to attached drawings, in which.

DETAILED DESCRIPTION

Figure 1:
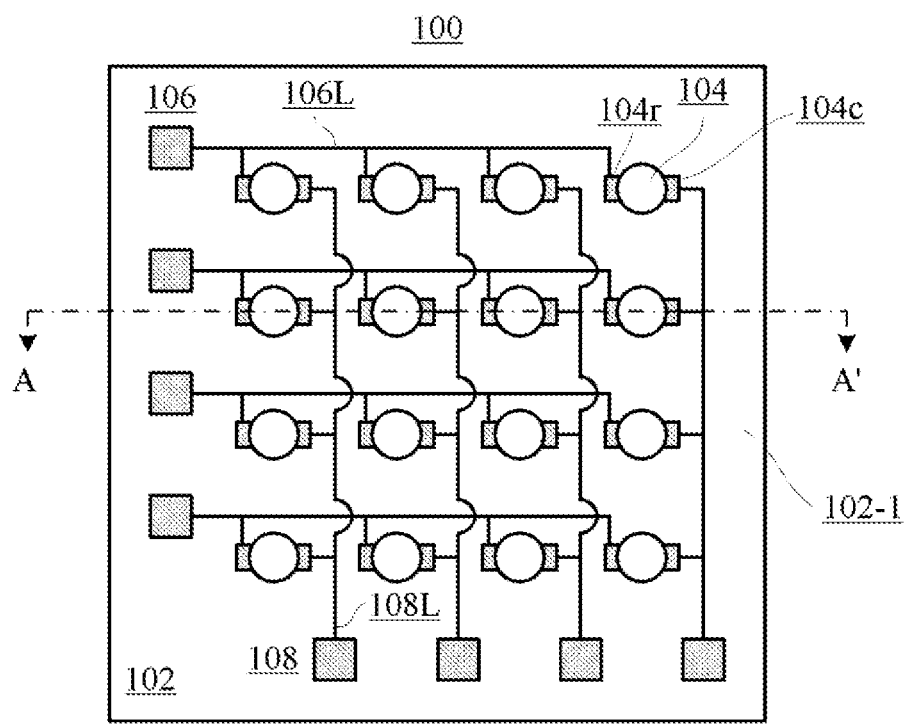
FIG. 1 schematically illustrates a top view of a particle screening device according to an embodiment of the present disclosure.

Hereinafter, descriptions are given for embodiments of the present disclosure with reference to the attached drawings. However, it is to be understood that these descriptions are illustrative and not intended to limit the present disclosure. Further, in the following, known structures and technology are not described to avoid obscuring concepts of the present disclosure unnecessarily.

In the drawings, various structures according to embodiments of the present disclosure are schematically shown. However, they are not drawn to scale, and some features may be enlarged while some features may be omitted for sake of clarity. Moreover, shapes and relative sizes and positions of regions and layers shown in the drawings are only illustrative, and deviations may occur due to manufacture tolerances and technique limitations in practice. Those skilled in the art can also devise regions/layers of other different shapes, sizes, and relative positions as desired.

In the context of the present disclosure, when a layer/element is recited as being "on" a further layer/element, the layer/element can be disposed directly on the further layer/element, or otherwise there may be an intervening layer/element interposed therebetween. Further, if a layer/element is "on" a further layer/element in an orientation, then the layer/element can be "under" the further layer/element when the orientation is turned.

In one embodiment of the present disclosure, a particle screening device for screening a target particle is provided. For example, a CTC can be screened from peripheral blood samples. The particle screening device may comprise a particle strainer. Specifically, the particle strainer may comprise a micropore array having a strainer shape which is formed on the substrate and penetrates through the substrate from a first side to an opposite second side of the substrate. Each micropore in the array has a size which is configured to at least permit particles having a smaller size than the target particle to flow through. Therefore, the size of the micropores can be determined according to, for example, size distribution of target particles.

In one embodiment, the size of the micropores can be configured to be larger than at least some target particles. Further, the size of the micropores can even be configured to be larger than all target particles. Therefore, particles having a size comparable with target particles can flow through the micropores and be screened. Generally, the size of the micropores can be configured to be comparable with or larger than that of target particles. For example, in a case wherein the target particles are CTCs, the micropores may have a size of about 100 nm-100 μm.

In an embodiment of the present disclosure, the device further comprises an electrode formed on at least one side of the first and second sides of the substrate and near at least some micropores, and the electrode is configured to generate an electric field at corresponding micropores. For example, the electric field can be determined by at least one of size and dielectric property of the target particles so as to achieve DEP of target particles in the electric field. Specifically, the target particles substantially cannot flow through the micropores because of acting of the DEP force, and for example, can be driven (such as attracted) to the micropores or the electrode. Other particles in the samples can flow through the micropores with very small or without DEP force, or with DEP force far away from the electrode. Therefore, screening specificity can be improved. On other hand, the target particles can be split by the electric field to detect materials therein.

Thus, even the micropores have a size comparable with or larger than that of the target particles, the target particles can be screened by DEP force rather than the micropores (for example, being attracted to the electrode). Further, particles having a size comparable with the target particles can flow through the micropores and be screened. Therefore, it is possible to distinguish the target particles from other particles having a comparable size.

The electrodes may be formed with respect to respective micropores, i.e., each micropore in the at least some micropores has a (group of) corresponding electrode. Respective electrode (group) in each micropore can be addressed by appropriate wiring. Alternatively, some or all the at least some micropores may share one electrode.

The electrodes may be configured in various means. For example, the electrodes may have a first electrode and a second electrode disposed and separated (for example, oppositely disposed) along periphery of corresponding micropore so that an electric field can be generated between the first and second electrodes. In such a case, especially in a case wherein the micropores are disposed in lines and columns, the wires for applying voltages to the first and second electrodes of respective micropore can be disposed in crossed lines and columns such that each micropore corresponds to a crossing of a line and a column. The first electrodes in micropores in the same line can be connected to one wiring (for example, a line wiring), and the second electrodes in micropores in the same column can be connected to one further wiring (for example, a column wiring). Therefore, by means of a line wiring and a column wiring, the micropore connected to the line wiring and the column wiring (i.e., the micropore corresponding to the crossing of the line wiring and the column wiring) can be individually addressed. Alternatively, the electrode may comprise a stack structure of a first electrode layer, a dielectric layer and a second electrode layer. In the stack structure, an electric field can be generated between the first electrode layer and the second electrode layer.

In an embodiment of the present disclosure, the device may comprise a microfluidic chip for introducing samples into the device, and specifically, for introducing samples into particle strainers for screening target particles.

The technology of the present disclosure can be implemented in various ways, some of which are exemplified in the following with reference to the drawings. It should be noted that CTCs are described as an example hereafter. However, the present disclosure is not limited thereto.

Figure 2:
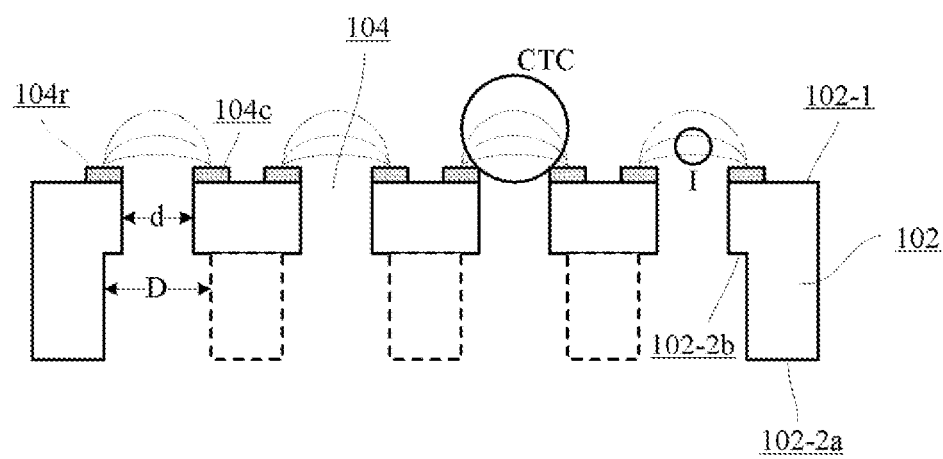
FIG. 2 schematically illustrates a cross-sectional view taken along line AA' in FIG. 1.

FIG. 1 schematically illustrates a top view of a particle screening device according to an embodiment of the present disclosure, and FIG. 2 schematically illustrates a cross-sectional view taken along line AA' in FIG. 1. It should be noted that FIG. 1 and FIG. 2 are not necessarily drawn to scale.

As shown in FIG. 1 and FIG. 2, the sensing device 100 according to the embodiment may comprise a substrate 102. For example, the substrate 102 may comprise at least one of semiconductor materials, such as silicon, inorganic materials, such as glass and quartz, and polymers, such as polymethyl methacrylate and polycarbonate. The substrate 102 has a first side 102-1 and a second side opposite to the first side 102-1 (102-2a and 102-2b in FIG. 2). An array of micropores 104 can be formed on the substrate 102. Each micropore 104 can penetrate through the substrate from the first side to the second side.

Though an array of 4×4 micropores is shown in FIG. 1, the present disclosure is not limited thereto. There may be more or less micropores. Further, the array in FIG. 1 is an array having a regular square shape. However, the present disclosure is not limited thereto. The micropores may be disposed in other regular or irregular patterns. The shapes of the micropores are not limited to the regular cylindrical shape shown in the drawings. The micropores may have any other shape, which is suited for manufacturing, and may comprise variations in shape caused by manufacturing tolerance, process limitation, etc.

In order to prevent the micropores 104 from being too large (so that particles are attached to side walls of the micropores 104 to increase the risk of blocking the micropores 104), the substrate can be thinned from the second side (indicated by 102-2b in FIG. 2) in the micropore array, such that the thinned portion 102-2b is recessed with respect to the periphery area 102-2a located in a peripheral area of the micropore array. In order not to reduce mechanical strength of the thinned substrate (especially in a case where the micropore array has a large size), only a portion of the substrate around the micropores is thinned instead of thinning the substrate in the whole micropore array, and portions of the substrate between micropores (indicated by dash lines in FIG. 2) keep unchanged. Thus, there may exist two cylindrical holes in the micropore. The cylindrical hole adjacent to the first side 102-1 is the micropore which is a strainer hole having a small size and screening target particles reliably. The cylindrical hole adjacent to the second side 102-2b is formed by thinning the substrate and has a large size so that the particles through the strainer hole can flow through it.

Therefore, the size of the micropores can be determined according to the size of target particles. For example, it has been found that human blood erythrocyte has a biconcave cake shape having a diameter of about 6 μm-8 μm with a thicker edge and a thinner middle portion, just like a ripe persimmon. Human blood leukocyte generally has a spherical shape and a diameter of about 10 μm-15 μm. However, most CTCs have a diameter larger than 15 μm. Therefore, the aperture d of the micropores 104 can be configured to be about 100 nm-100 μm. The aperture D of the cylindrical hole adjacent to the second side can be configured to be about 30-40 μm. The micropores in the array can be configured in the same manner.

Of course, the micropores can be configured differently according to the target particles to be screened. A further strainer having a larger size before the strainer (the substrate and the micropore 104) can be disposed to screen particles larger than the target particles. Strainers can be disposed in multiple stages sequentially arranged by micropore size in descending order, and each strainer can screen particles having a size corresponding to respective micropore. Alternatively, the strainer can be detachably installed to the particle screening device such that it can be replaced by another strainer having a different size so as to screen different target particles.

Electrodes (104r and 104c) can be formed around the micropore 104. For example, an electric field can be generated at the micropores 104 by applying a voltage to the electrodes, as indicated by dash lines between electrodes 104r and 104c in FIG. 2. Though electrodes (104r and 104c) are formed around each micropore 104 as shown in FIG. 1, the present disclosure is not limited thereto. For example, electrodes can be just formed around some micropores.

In addition, in the example as shown in FIG. 1, each micropore 104 has a group of electrodes 104r and 104c disposed along periphery thereof. The electrodes 104r and 104c can be disposed oppositely (i.e., the line connecting centers of the electrodes substantially coincides with respective diameter of the micropore 104). However, the configuration of electrodes is not limited thereto. For example, the electrodes 104r and 104c may not be disposed oppositely, as long as they are separated each other such that voltages can be applied to them respectively to generate an electric field therebetween. The electrode group of respective micropore is not limited to two electrodes 104r and 104c, and more electrodes can be disposed along periphery of the micropore. Further, it is not limited in the present disclosure that each micropore has an individual electrode group, and some micropores may share a common electrode group. For example, the electrodes 104r and 104c may continuously extend without being disconnected between adjacent micropores as shown in the drawing.

Those skilled in the art shall understand that any electrode configuration can be employed as long as an electric field can be generated at the micropores.

Wirings (106L and 108L) can be disposed on the substrate 102 so as to applying voltages to respective electrodes. In the example as shown in FIG. 1, wirings 106L are disposed in lines so as to apply voltages to electrodes 104r of micropores, and wirings 108L are disposed in columns so as to apply voltages to electrodes 104c of micropores. Each wiring 106L may be connected to a voltage-applying pad 106, and a voltage can be applied to the electrode 104r by the voltage-applying pad 106 through the wiring 106L. Each wiring 108L can be connected to a bonding pad 108, and a voltage can be applied to the electrode 104c by the bonding pad 108 through the wiring 108L. In such a case, the electrode group of respective micropore can be addressed individually. For example, if an electrode group of a micropore at the crossing of a certain line and a certain column will be addressed, a voltage can be applied to the electrode 104r of the micropore by the wiring 106L corresponding to the line, and a voltage can be applied to the electrode 104c of the micropore by the wiring 108L corresponding to the column.

The electrode and the wiring may comprise conducting materials, for example, metals, such as Au, Ti, Pt, etc.

A direct or alternating voltage can be applied to the electrodes 104r and 104c via the bonding pads 106 and 108. For example, the applied voltage may have an amplitude of about 0-100V, and may have a frequency of about 0 Hz-200 MHz in case of an alternating voltage. Therefore, an electric field (especially a non-uniform electric field) can be generated at the corresponding micropore 104, such that electrical manipulation of particles can be achieved. According to the embodiment of the present disclosure, manipulation of particles, such as capturing, releasing, locating, etc., can be achieved based on the Dielectrophoresis (DEP) technique by means of such an electric field.

DEP refers to such a phenomenon in which, in an (non-uniform) electric field, charges may be induced from particles (such as biological cells or other particles) suspending in medium due to polarization on surfaces of the particles, such that the particles may have translational movements due to interaction between the charges and the (non-uniform) electric field. Quantitatively, for a spherical particle having a radius r, the DEP force in the (non-uniform) electric field is:

$$F = 2\pi r^3 \varepsilon_m \mathrm{Re}[f_{CM}(\omega)] \nabla |E|^2$$

wherein Re[ ] indicates taking a real part, r is the radius of the particle, $\varepsilon_m$ is the relative dielectric constant of the medium, in which the particle suspends, $\omega$ is the frequency of the applied electric field, and E is the intensity of the electric field. The factor of $f_{CM}(\omega)$ is referred as Clausius-Mossotti factor, and is defined as:

$$f_{CM}(\omega) = \frac{\varepsilon_p^* - \varepsilon_m^*}{\varepsilon_p^* + 2\varepsilon_m^*}$$

wherein $\varepsilon^*_p$ and $\varepsilon^*_m$ are the complex dielectric constants of the particle and the suspending medium, respectively, and the equation of $\varepsilon^* = \varepsilon - j\sigma/\omega$ is satisfied, wherein $\varepsilon$ and $\sigma$ are the real dielectric constant and the real electric conductivity, respectively, and j is the imaginary unit.

Figure 4:
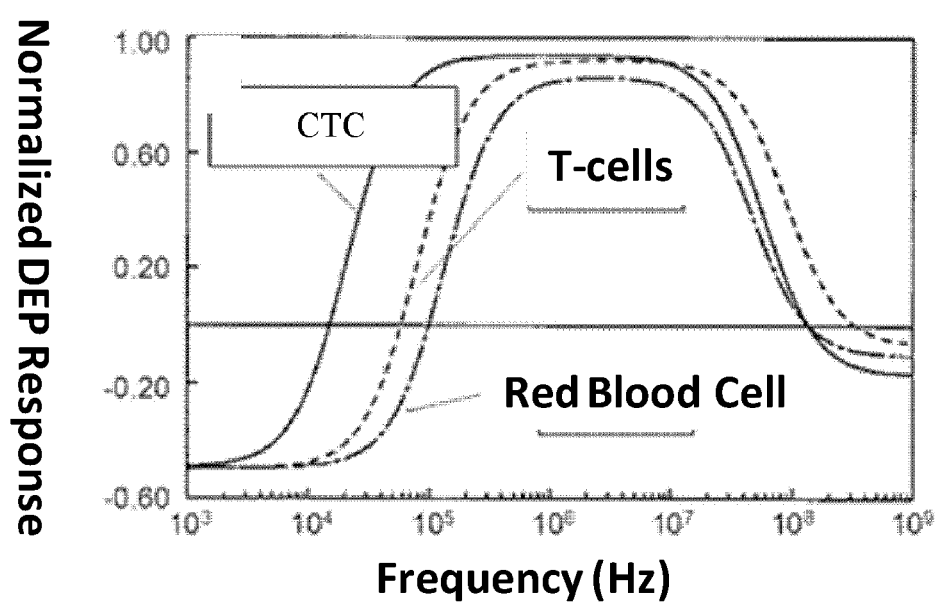
FIG. 4 illustrates dielectrophoresis (DEP) response for different cells.

As can be seen from the equation above, the DEP force acted on a particle in an electric field relates to the size of the particle (r), dielectric property of the particle ($\varepsilon$ and $\sigma$), etc. with other conditions being the same. CTCs are different from normal cells in size. Further, CTCs have specificity in dielectric property ($\varepsilon$ and $\sigma$) due to their differences from normal cells in surface morphology, structure, membrane protein, etc. FIG. 4 illustrates normalized dielectric response in different frequencies of an electric field for tumor cells (CTCs), T cells and erythrocyte. It can be seen that there exists significant difference among them. For example, when the applied electric field has a frequency of about 60-80 kHz, the tumor cells are subjected a relative large DEP force (attraction), while the T cells are subjected a DEP force approximately close to zero.

Therefore, the applied electric field can be determined by at least one of size and dielectric property of target particles, so as to manipulate the target particles by means of DEP. For example, the electric field can be configured such that the target particles are attracted to the micropores or electrodes so as to improve enriching of the target particles. FIG. 2 illustrates such a case in which CTCs having a large size stay at the micropores due to barrier of the strainer hole 104 and the pushing-away DEP force from the electrodes, while other particles having smaller size flow through the strainer hole 104 without a DEP force or with smaller DEP force or with a pushing-away DEP force from the electrodes.

It should be noted that only a configuration of the substrate, the wirings and the electrodes is illustrated in FIG. 1 and FIG. 2. However, there may also exist other layers. For example, a dielectric layer may be formed between the substrate and the electrodes and the wirings. A dielectric layer may be formed at the crossing of the wirings. Further, a passivation layer may be formed on surfaces of the substrate and the wirings.

In addition, in the example of FIG. 1 and FIG. 2, electrodes and wirings are only formed on the first side 102-1. However, the present disclosure is not limited thereto. The electrodes and wirings may also be formed on the second side (102-a and 102-b) (as the first side). Alternatively, the electrodes and wirings can be formed on different sides. For example, the electrodes can be formed on the first side 102-1, while the wirings can be formed on the second side (102-a and 102-b), vice versa. And they can be electrically connected by through vias.

For those skilled in the art, the electrodes and the wirings can be formed on the substrate (for example, the silicon substrate) by various means. The present disclosure is not limited to specific forms of the electrodes and wirings.

Figure 6:
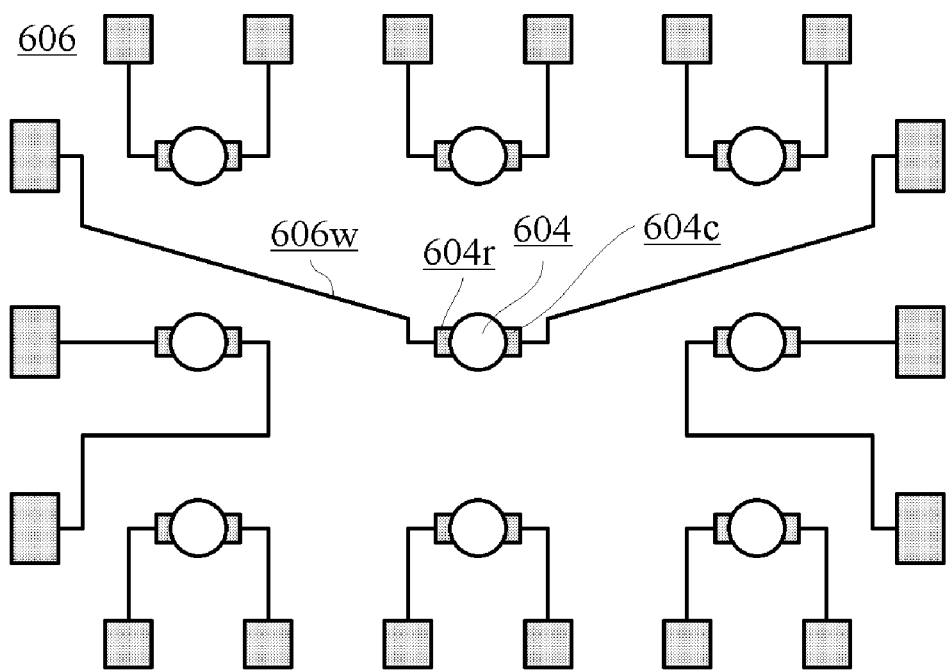
FIG. 6 schematically illustrates a cross-sectional view of a wiring layout according to a further embodiment of the present disclosure.

FIG. 6 schematically illustrates layout of wirings according to a further embodiment of the present disclosure. In the example, for electrodes 604r and 604c of each micropore 604, respective bonding pads 606 are disposed. The bonding pads 606 are disposed along periphery of the array of the micropores 604, and are connected to the electrodes 604r and 604c of respective micropore 604 by corresponding wires 606w.

Figure 3:
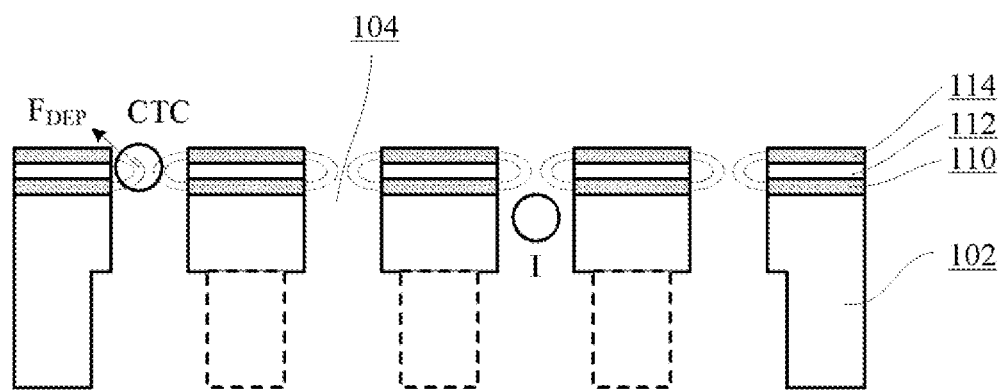
FIG. 3 schematically illustrates a cross-sectional view of an electrode structure according to a further embodiment of the present disclosure.

FIG. 3 schematically illustrates a cross-sectional view of an electrode structure according to a further embodiment of the present disclosure.

In the example, the components which are the same as those in the embodiment above are indicated by the same reference numbers except for the electrode structure. Hereafter, the electrode structure will be described.

As illustrate in FIG. 3, the electrode may be a stack structure of a first electrode layer 110, a dielectric layer 112 and a second electrode layer 114. By applying a voltage to the first electrode layer 110 and the second electrode layer 114, respectively, an electric field may be formed therebetween, as indicated by dash lines in FIG. 3. Those skilled in the art may conceive various configurations to form wirings for the first electrode layer 110 and the second electrode layer 114, which are not shown in the drawings.

In the example of FIG. 3, the electrodes are shown to be continuous between adjacent micropores. However, the present disclosure is not limited thereto. For example, the electrode (the stack structure of the first electrode layer 110, the dielectric layer 112 and the second electrode layer 114) can be disconnected between adjacent micropores. Therefore, one or more micropores may have a corresponding individual electrode, such that the individual electrode for the one or more micropores can be addressed individually.

Therefore, the applied electric field can be determined by at least one of size and dielectric property of target particles, so as to manipulate the target particles by means of DEP. For example, the electric field can be configured such that the target particles are abstracted to the micropores or electrodes so as to improve enriching of the target particles. FIG. 3 illustrates such a case in which CTCs having a small size are attracted at the micropores due to the DEP force $F_{DEP}$ when they are flowing through the strainer hole 104; However, other particles I having a small size flow through the strainer hole 104 because they don't experience a DEP force or, only experience a small DEP force or with a DEP force to push them away from the electrodes.

According to embodiments of the present disclosure, the electrode can be used to achieve DEP, and further can be used to sort target particles. For example, cell sorting is a critical step for analyzing materials inside cells (nucleic acid, protein, small signaling molecule). The cell membrane of a bi-layer structure generally has high electric impedance. And the cell exposed in an electric field may generate a transmembrane potential on both sides of the cell membrane. If the transmembrane potential is higher than 1V, the cell membrane may be broken down and the cell may be lysed. For example, the inventor has found that if the conductivity of the cell buffer solution is 0.01 S/m, the cell membrane of the tumor cell shall be broken down rapidly by applying an electric field over 2 kV/cm at a frequency of 1 MHz, and the cell is lysed.

According to the embodiment of the present disclosure, electric lysis of cells can be selectively achieved by applying an appropriate voltage to the electrodes. In addition, materials inside the lysed CTCs can be collected by micro-fluidic chip to provide experimental materials for further analysis.

Figure 5:
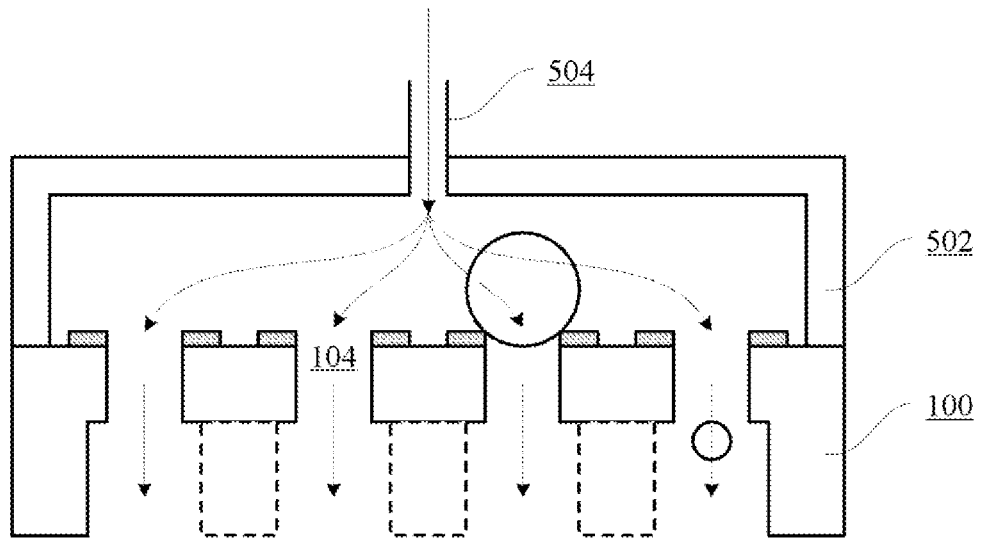
FIG. 5 schematically illustrates a cross-sectional view of a particle screening device according to a further embodiment of the present disclosure.

FIG. 5 schematically illustrates a cross-sectional view of a particle screening device according to a further embodiment of the present disclosure.

As shown in FIG. 5, the particle screening device comprises the device 100 above and a microfluidic chip 502. The micro-fluidic chip 502 can comprise an opening 504 for introducing fluid samples including target particles into the device such that the target particles can be screened by the device 100.

The micro-fluidic chip can precisely control and manipulate fluid in micro-scale. For example, the micro-fluidic chip may be manufactured of transparent polymers, such as Polymethylmethacrylate (PMMA), Polycarbonate (PC), Polydimethylsiloxane (PDMS), etc., and may have microstructures, such as micro-pipes, micro-cavities, etc., manufactured by micro-fabrication technique. The micro-structures have at least one dimension in micro-scale among scales such as length, width, height, etc. A closed channel can be formed by bonding or by applying pressure to the micro-fluidic chip 502 with the device 100, so as to transport fluid.

Various features are described in different embodiments in the above descriptions. However, it is not implied that these features cannot be combined advantageously.

In the above, embodiments of the present disclosure are described. However, such embodiments are given for illustrative only, rather than limiting the scope of the present disclosure. The scope of the present disclosure is defined by appended claims and equivalents thereof. Without departing from the scope of the present disclosure, those skilled in the art can make various alternations and modifications which fall within the scope of the present disclosure.

The invention claimed is:
1. A particle screening device, comprising:
   a substrate including a first side and a second side opposite to the first side;
   a micropore array formed on the substrate, wherein each micropore penetrates through the substrate from the first side to the second side and has a size configured to at least permit particles smaller than target particles to flow into the micropore at the first side of the substrate, through the micropore, and flow out of the micropore at the second side of the substrate; and
   electrodes formed on at least one side of the first and second sides of the substrate and around at least some micropores, wherein the electrodes are configured to generate an electric field at corresponding micropores so as to achieve DEP of the target particles in the electric field, such that the target particles are attracted to and captured at the micropores while the particles smaller than the target particles flow out of the micropore at the second side of the substrate.

2. The particle screening device of claim 1, wherein the substrate comprises at least one of silicon, glass, quartz and polymer.

3. The particle screening device of claim 1, wherein the micropores have a size configured to be larger than at least some target particles.

4. The particle screening device of claim 1, wherein the target particles comprise CTCs.

5. The particle screening device of claim 4, wherein the micropores have a size of about 100 nm-100 µm.

6. The particle screening device of claim 1, wherein the electric field is determined by at least one of the size and the dielectric property of the target particles so as to achieve DEP of the target particles in the electric field.

7. The particle screening device of claim 1, wherein the electrodes are configured to be applied a direct voltage or an alternating voltage.

8. The particle screening device of claim 7, wherein the applied voltage has an amplitude of 0V-100V, and the applied alternating voltage has a frequency of 0 Hz-200 MHz.

9. The particle screening device of claim 1, wherein the electrodes are configured to be applied a voltage to lyse the target particles.

10. The particle screening device of claim 1, wherein the electrodes comprise a first electrode and a second electrode disposed and separated along a periphery of a corresponding micropore, and wherein the first and second electrodes are configured to generate an electric field therebetween.

11. The particle screening device of claim 10, further comprising wirings for applying voltages to the first and second electrodes respectively.

12. The particle screening device of claim 11, wherein the micropores in the array are arranged by lines and columns, and wherein the first electrodes of the micropores in the same line are connected to one wiring, and the second electrodes of the micropores in the same column are connected to one further wiring.

13. The particle screening device of claim 10, further comprising:

bonding pads for applying voltages to the first and second electrodes at respective micropores; and wirings formed between respective bonding pads and corresponding electrodes.

14. The particle screening device of claim 1, wherein the electrodes have a stack structure of a first electrode layer, a dielectric layer and a second electrode layer, and wherein the stack structure is configured to generate an electric field between the first electrode layer and the second electrode layer.

15. The particle screening device of claim 1, wherein the electrodes are formed with respect to respective micropores, and the electrode of each micropore can be addressed individually.

16. The particle screening device of claim 1, further comprising a micro-fluidic chip which is configured to introduce fluidic samples containing the target particles.

* * * * *